United States Patent [19]
Goodwin et al.

[11] Patent Number: 6,107,030
[45] Date of Patent: Aug. 22, 2000

[54] DETERMINING ORIENTATION AND DIRECTION OF DNA SEQUENCES

[75] Inventors: Edwin H. Goodwin; Julianne Meyne, both of Los Alamos, N. Mex.

[73] Assignee: The Regents of the University of California, Los Alamos, N. Mex.

[21] Appl. No.: 08/790,402

[22] Filed: Jan. 29, 1997

[51] Int. Cl.[7] ........................ C12Q 1/68
[52] U.S. Cl. ........................ 435/6
[58] Field of Search ........................ 435/6

[56] References Cited

PUBLICATIONS

E.H. Goodwin and J. Meyne, "Strand–Specific FISH Reveals Orientation Of Chromosome 18 Alphoid DNA," Cytogenet. Cell Genet. 63, 126 (1993).
E.H. Goodwin, J. Meyne, S.M. Bailey, D. Quigley, "On the Origin of Lateral Asymmetry," Chromosoma 104, 345 (1996).
Epstein, L. et al., 1995, Cytometry, vol. 21, pp. 378–381.
Lehninger, A., 1975, Biochemistry, Second Ed., Worth Publishers, Inc., especially p. 873.

*Primary Examiner*—James Ketter
*Assistant Examiner*—Irem Yucel
*Attorney, Agent, or Firm*—Samuel M. Freund

[57] ABSTRACT

Determining orientation and direction of DNA sequences. A method by which fluorescence in situ hybridization can be made strand specific is described. Cell cultures are grown in a medium containing a halogenated nucleotide. The analog is partially incorporated in one DNA strand of each chromatid. This substitution takes place in opposite strands of the two sister chromatids. After staining with the fluorescent DNA-binding dye Hoechst 33258, cells are exposed to long-wavelength ultraviolet light which results in numerous strand nicks. These nicks enable the substituted strand to be denatured and solubilized by heat, treatment with high or low pH aqueous solutions, or by immersing the strands in 2×SSC (0.3M NaCl+0.03M sodium citrate), to name three procedures. It is unnecessary to enzymatically digest the strands using Exo III or another exonuclease in order to excise and solubilize nucleotides starting at the sites of the nicks. The denaturing/solubilizing process removes most of the substituted strand while leaving the prereplication strand largely intact. Hybridization of a single-stranded probe of a tandem repeat arranged in a head-to-tail orientation will result in hybridization only to the chromatid with the complementary strand present.

10 Claims, 2 Drawing Sheets

DETERMINING ORIENTATION AND DIRECTION OF DNA SEQUENCES

FIELD OF THE INVENTION

The present invention relates generally to the study of the molecular organization and mapping of chromosomes and, more particularly, to the detection of the location of DNA sequences in chromosomes, the 5'-to-3' direction of these sequences, and their orientation relative to other such sequences using chromosome-orientation fluorescence in situ hybridization. This invention was made with government support under Contract No. W-7405-ENG-36 awarded by the U.S. Department of Energy to The Regents of The University of California. The government has certain rights in the invention.

BACKGROUND OF THE INVENTION

Fluorescence in situ hybridization (FISH) has proven to be a valuable tool for cytogenetic research. The procedure reveals the chromosomal location of DNA target sequences with homology to labeled nucleic acid probes. As an example, inversions in DNA sequences are known to be associated with tumors and birth defects. Since hybridization is dependent on nucleotide pairing through hydrogen bonding, it requires that both probe and target be functionally single stranded initially. Probes may be either single stranded at the time of their construction or made single stranded by denaturation with heat or a high or low pH. When the target is double stranded, such as the DNA of chromosomes, denaturation is also required prior to hybridization. With FISH, this is most commonly done by thermal denaturation. Enzymatic digestion with exonuclease III (Exo III) has also been used to obtain a single-stranded target.

Therefore, preparation of single-stranded chromatids for determination of chromosomal orientation and strand direction of DNA sequences is receiving increased attention. Conventional fluorescence in situ hybridization methods rely on nucleotide base pairing between a labeled probe and the complementary chromosomal target sequence. Both probe and target DNAs must be functionally single-stranded at the start of the procedure. Single-stranded probes can be constructed or prepared, but the chromosomal DNA must be made single-stranded by denaturation. Because both strands are present in both chromatids of each chromosome, even single-stranded probes will hybridize to both chromatids of the target chromosome.

Selectively removing one strand of the DNA double helix from each chromatid makes strand-specific fluorescence in situ hybridization (FISH) possible. Single-stranded probes can then be hybridized to single-stranded chromosomal DNA without denaturation. Probes of repetitive sequences arranged head-to-tail in tandem arrays will hybridize only to one chromatid. By contrast, probes of ubiquitous repeat sequences, such as Alu, that are present in both directions on each DNA strand, will hybridize to both chromatids. Thus, the method reveals the orientation of repetitive sequences and has been designated as CO-FISH for chromosome orientation-FISH. This process is schematically illustrated in FIGS. 1a–e hereof, labeled Prior Art, and is reported in "Strand-Specific FISH Reveals Orientation Of Chromosome 18 Alphoid DNA," by E. H. Goodwin and J. Meyne, Cytogenet. Cell Genet., 63, 126 (1993), the teachings of which are hereby incorporated by reference herein.

In its broadest embodiment, the manner in which FISH can be made strand specific of Goodwin et al., supra, may be understood as follows. First, cell cultures are grown in a medium containing a halogenated nucleotide analogue such as bromodeoxyuridine (BrdU) (FIG. 1a). Due to the semi-conservative nature of DNA synthesis, the two newly replicated chromatids are singly substituted; that is, the nucleotide analogue is partially substituted for thymidine in one DNA strand of each chromatid (FIG. 1b). Nucleotide analogue incorporation takes place in opposite strands of the two sister chromatids; each replicated chromosome now containing sister chromatids that are singly substituted in opposite DNA strands. Metaphase chromosome spreads are prepared by standard methods. After staining with the fluorescent DNA-binding dye Hoechst 33258, cells are exposed to long-wavelength ultraviolet light which results in numerous strand breaks that are thought to occur preferentially at nucleotide analogue incorporation sites. Nicks produced in chromosomal DNA by this treatment are substrates for enzymatic digestion by Exo III which excises nucleotides from one strand of double-stranded DNA starting at the sites of the nicks. In theory, the process should remove most of the nucleotide analogue incorporated strand while leaving the original (prereplication) strand largely intact (FIG. 1c). The single strands remaining in each of the two chromatids are complementary. Thus, chromatids can not only be made single stranded, but the sister chromatids contain only complementary DNA strands. Hybridization of a single-stranded probe of a tandem repeat arranged in a head-to-tail orientation will result in hybridization only to the chromatid with the complementary strand present (FIG. 1d). Finally, detection of the hybridization site will demonstrate fluorescence on only one chromatid (FIG. 1e).

Slides prepared for the CO-FISH method can also be used to determine the direction of the DNA strand to which the single-stranded probe hybridizes. This procedure is referred to as chromosome orientation and direction FISH, or COD-FISH, and is schematically illustrated in FIG. 2a,b hereof, labeled Prior Art. The C-rich telomere probe is co-hybridized with a single-stranded probe of the sequence of interest (FIG. 2a). Because the G-rich telomere sequence is located at the 3' end of the DNA strand, the C-rich strand probe determines the 3' end of the DNA strands in each chromatid. The sequence of interest will hybridize to its complementary sequence. The 5'-to-3' direction of each strand can be determined by the position of the telomere fluorescence (FIG. 2b). The direction of the sequence of interest can be inferred from this information.

Multiple color and sequential hybridizations can be used on CO-FISH slides. Two or more single-stranded probes with different molecular tags can be hybridized at once, in a similar manner to that for standard FISH methods. Sequential hybridizations are simple. After the first hybridization, the slide is rinsed in 2× SSC (0.3 M NaCl+0.03 M sodium citrate) to remove any excess probe from the slide and then drained to remove excess 2× SSC, but not allowed to dry. The strand may then be again hybridized with another probe. Sequential hybridizations are preferred for two color hybridizations with complementary strands of repeat probes. Four sequential hybridizations have been achieved by the present inventors on a single slide. It is believed that the only limitation is the background hybridization after detection of the signal. However, this problem may be reduced by using probes labeled directly with fluorescent nucleotides rather than immunofluorescence detection. Essentially any method useful for in situ hybridization is applicable to the CO-FISH method.

Bromodeoxycytidine, the cytidine analogue was observed to produce similar results to BrdU.

Accordingly, it is an object of the present invention to prepare single stranded sister chromatids containing only complementary DNA strands without the use of an exonuclease.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for determination of chromosomal orientation and strand direction of DNA sequences may include the steps of: preparing a cell sample in which one strand of the DNA of some cells in the cell sample has a halogenated nucleotide analogue such as BrdU or BrdC substituted for thymidine or deoxycytidine, respectively, at many sites; selectively removing the halogenated nucleotide analogue-substituted DNA strand from the double helix by the steps of inducing breaks in the halogenated nucleotide analogue-substituted strand; and denaturing and solubilizing the halogenated nucleotide analogue-substituted strand, whereby the unsubstituted strand is left intact; hybridizing a single-stranded probe to the unsubstituted strand; and detecting the chromosomes.

Benefits and advantages of the present invention include replacement of the expensive and unfamiliar exonuclease digestion process for removing broken halogenated nucleotide analogue-substituted DNA strands with more familiar, less expensive and less time-consuming denaturation/solubilization processes.

BRIEF DESCRIPTION OF THE DRAWINGS

The accompanying drawings, which are incorporated in and form a part of the specification, illustrate the prior art and, together with the description, serve to explain the principles of the present invention. In the drawings.

DETAILED DESCRIPTION

Figure 1:
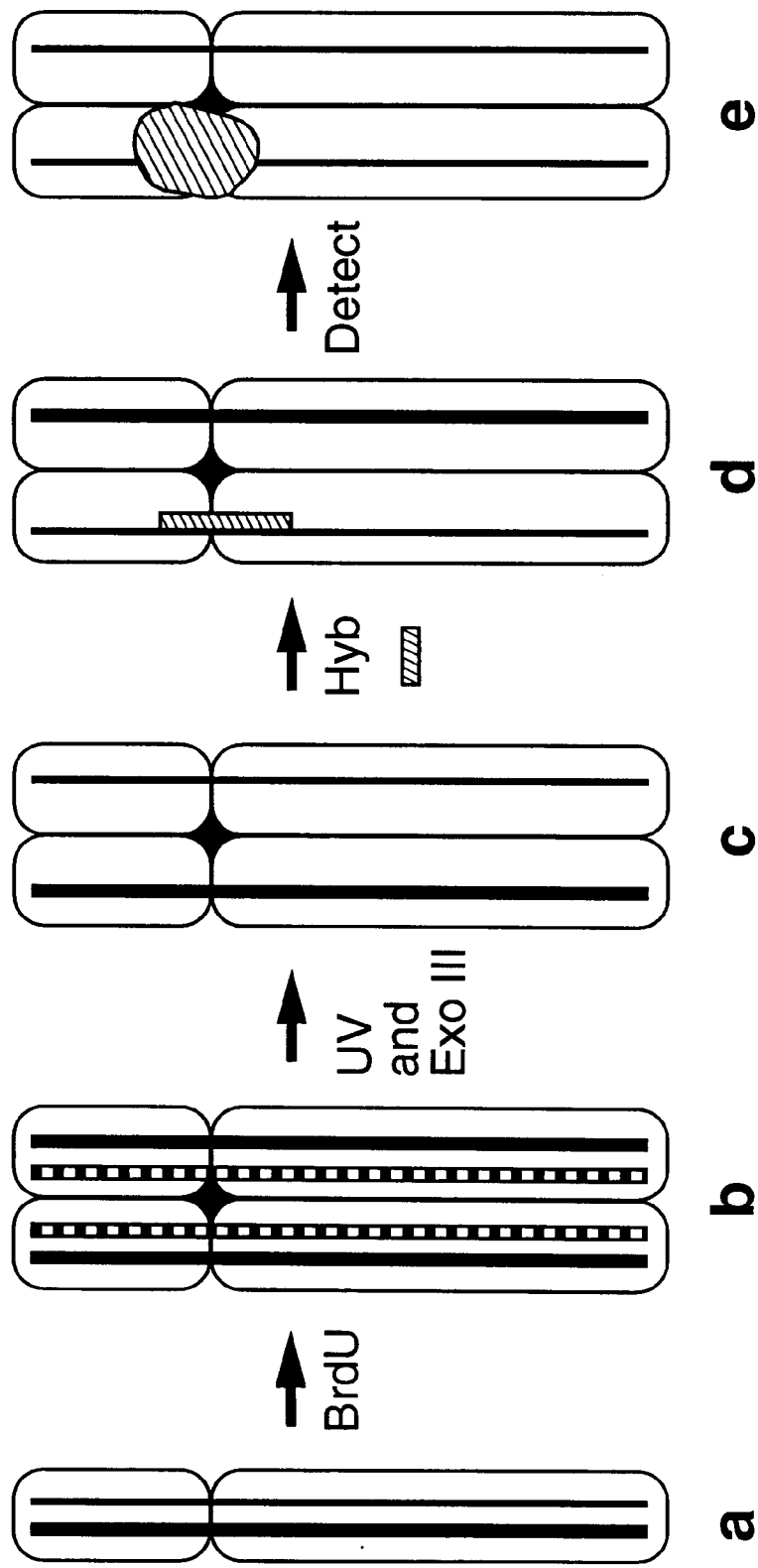
FIGS. 1a–e illustrate the removal of one strand of the DNA double helix from each chromatid in the preparation of single-stranded chromosomal DNA without denaturation, and the hybridization of a probe of repetitive sequences arranged head-to-tail in tandem arrays to one chromatid according to the strand-specific chromosome orientation fluorescence in situ hybridization method of the prior art.
Figure 2:
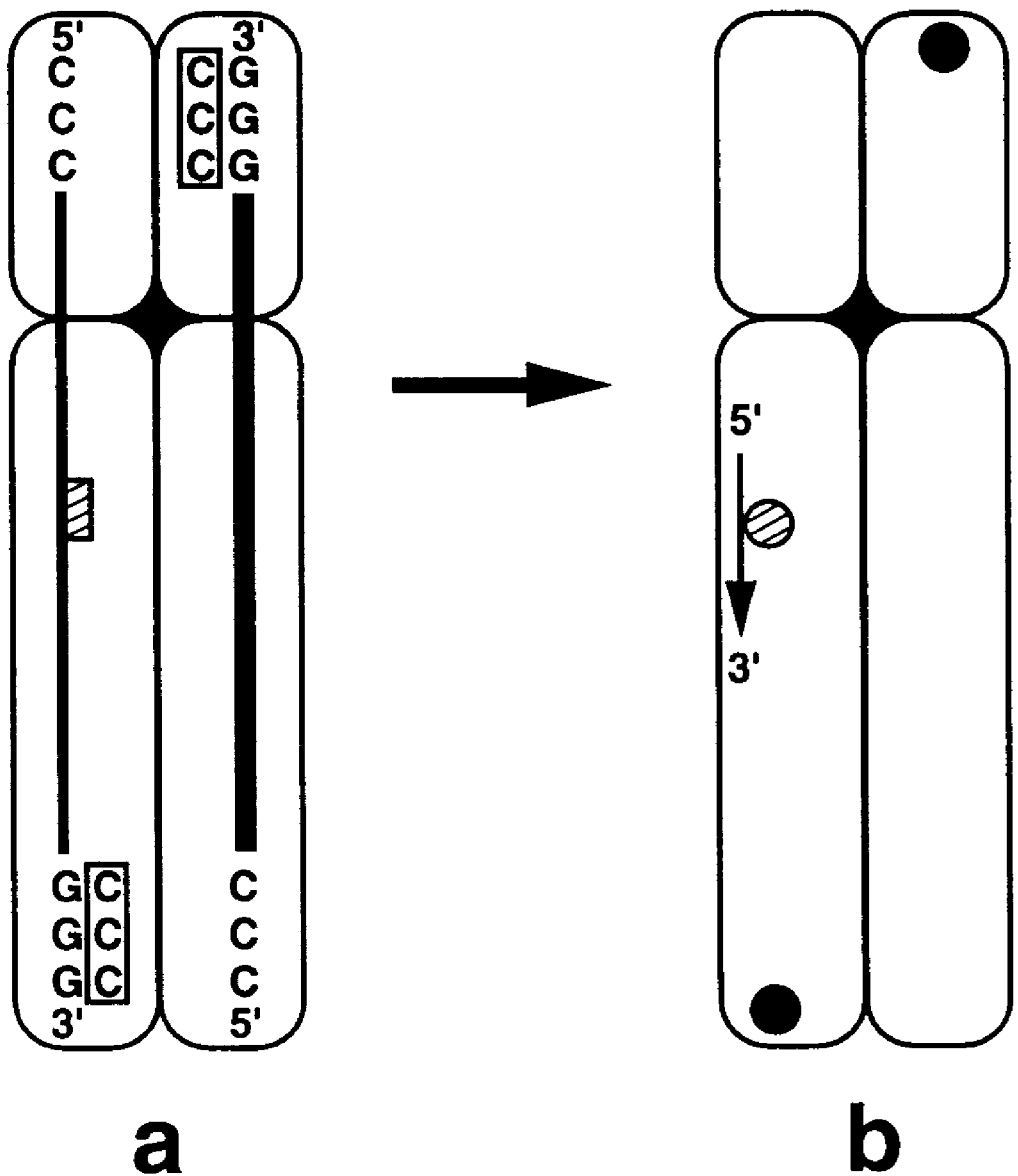
FIGS. 2a,b illustrate the use of the chromosome orientation fluorescence in situ hybridization method for determining the direction of the DNA strand to which a single-stranded probe hybridizes of the prior art.

Briefly, the present invention includes a method by which fluorescence in situ hybridization can be made strand specific. First, cell cultures are grown in a medium containing a halogenated nucleotide analogue. The two newly replicated chromatids are singly substituted; that is, the nucleotide analogue is partially incorporated in one DNA strand of each chromatid, replacing the natural nucleotide at these locations. This substitution takes place in opposite strands of the two sister chromatids; each replicated chromosome now containing sister chromatids that are singly substituted in opposite DNA strands. Metaphase chromosome spreads are prepared by standard methods. After staining with the fluorescent DNA-binding dye Hoechst 33258, cells are exposed to long-wavelength ultraviolet light which results in numerous strand nicks that are thought to occur preferentially at the incorporation sites. Nicks produced in chromosomal DNA by this treatment enable the substituted strand to be denatured and solubilized by heat or treatment with high or low pH aqueous solutions, to name two procedures. It is unnecessary to enzymatically digest the strands using Exo III or another exonuclease, as described in the prior art, in order to excise and solubilize nucleotides from one strand of double-stranded DNA starting at the sites of the nicks. The denaturing/solubilizing process removes most of the substituted strand while leaving the original (prereplication) strand largely intact. The single strands remaining in each of the two chromatids are complementary. Thus, chromatids can not only be made single stranded, but the sister chromatids contain only complementary DNA strands. Hybridization of a single-stranded probe of a tandem repeat arranged in a head-to-tail orientation will result in hybridization only to the chromatid with the complementary strand present, and detection of the hybridization site will demonstrate fluorescence on only one chromatid.

Having generally described the invention, the following EXAMPLE provides more detail concerning the practice thereof.

EXAMPLE

In what follows, typical, successfully applied and tested protocols are described for the various procedures.

A. Mitotic Cell Collection: The objective of this part of the procedure is to obtain cells with condense mitotic chromosomes that have one strand of the DNA double helix where BrdU (bromodeoxyuridine) has been incorporated in place of thymidine at several sites in the strand. The process will work with any cell line. Also, as stated above, bromodeoxycytidine works just as well as bromodeoxyuridine.

i. Cell Culture: Plateau-phase normal human fibroblasts are subcultured into medium containing $10^{-5}$ M BrdU. After 26 hours, Colcemid (0.1 µg/ml) is added to the medium for an additional 4 hours. Colcemid blocks cells in mitosis. The culture is harvested by trypsinization.

ii. Microscope slide preparation: Cells are suspended in hypotonic KCl (75 mM) for 15 minutes and fixed in 3:1 methanol:acetic acid. Fixed cells are dropped onto cold wet microscope slides and allowed to dry.

B. Preparation of single-stranded target DNA: The objective of this part of the procedure is to selectively remove the BrdU-incorporated strand from the double helix.

i. Inducing breaks in the BrdU-substituted strand: A photochemical reaction is induced by the absorption of uv light by BrdU. The reaction causes single-strand breaks in the BrdU-incorporated strand of the DNA double helix, but not in the unsubstituted strand. Hoechst 33258 is a well-known dye that binds to DNA and shifts the uv absorption spectrum to longer, more readily available wavelengths.

Microscope slide preparations are stained in 0.5 µg/ml Hoechst 33258 for 15 minutes at room temperature and then rinsed briefly in distilled $H_2O$. Two drops of 2× SSC (0.3M NaCl+0.03M sodium citrate) are placed on each slide and a 22×50 mm glass coverslip is placed on top. Slides are exposed to long-wave ultraviolet light (354 nm) for 30 minutes. Coverslips are removed, slides are rinsed in distilled $H_2O$ and allowed to dry.

ii. Removing (solubilizing) the BrdU-substituted strand: According to the prior art (Goodwin et al., supra) chromosomal DNA is subjected to enzymatic digestion with 3 units/μl of Exo III prepared in reaction buffer. Reaction buffer can be any solution where the enzyme performs at or near optimum activity. Fifty μl of enzyme are placed onto each slide, and the slide is covered with a 22×50 mm glass coverslip. After 5 minutes at room temperature, slides are rinsed in distilled H₂O and allowed to dry. Prior to the present discovery, it was believed by the inventors that this was the sole method for denaturing and solubilizing these unwanted strands, while leaving the original DNA untouched.

According to the teachings of the present invention, when the chromosomal DNA is denatured (melted), the small fragments from the BrdU-incorporated strand (which already has numerous breaks) diffuse away leaving behind the unsubstituted strand. The three methods described hereinbelow proceed by melting off the small fragments formed by the single-strand breaks and dissolving them. These methods have the advantages that no enzymatic treatment is needed and that the procedures are already familiar to cytogeneticists, who are the individuals using the technique.

a. Slides are thermally denatured in 70% formamide/2× SSC at 70° C. for 2 minutes, then rinsed in distilled H₂O and allowed to dry.

b. Slides are immersed in a high pH aqueous solution for 5 minutes (pH 11 works well) at room temperature then rinsed in distilled H₂O and allowed to dry. It is expected that low pH aqueous solutions will also be effective for this purpose.

c. Slides are immersed in 2× SSC at 60° C. for 30 minutes, then rinsed in distilled H₂O and allowed to dry.

C. In situ hybridization and fluorescence detection: A single-stranded nucleic acid probe (DNA or RNA) is hybridized to chromosomes made single-stranded by one of the methods described above. Synthetic oligomers to which a tail of labeled nucleotides has been added using terminal transferase are typically used. A hybridization mix containing 0.4 μg/ml probe DNA in 10–30% formamide, 2× SSC, and 500 μg/ml E. coli carrier DNA is applied to the slides. After hybridization overnight at 37° C., the slides are washed in 2× SSC at 42° C. Fluoresceinated avidin and a single round of amplification with anti-avidin antibody are used to detect hybridization of the probe. Chromosomes are counterstained with propidium iodide or 4,6-diamidino-2-phenylindole (DAPI) in antifade solution and viewed with a fluorescence microscope.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determination of chromosomal orientation and strand direction of DNA sequences, which comprises the steps of:

a. preparing a cell sample in which some cells have chromosomes in which a halogenated nucleotide analog has been incorporated into one strand of the DNA double helix;

b. selectively removing the halogenated nucleotide analogue-substituted strand from the double helix by the steps of:

i. inducing breaks in the halogenated nucleotide analogue-substituted strand; and ii. denaturing the halogenated nucleotide analogue-substituted strand, whereby the halogenated nucleotide analogue-substituted strand is solubilized and the unsubstituted strand is left intact;

c. hybridizing a single-stranded probe to the unsubstituted strand; and d. detecting the probe.

2. The method for determination of chromosomal orientation and strand direction of DNA sequences as described in claim 1, wherein said step of denaturing/solubilizing the halogenated nucleotide analogue-substituted strand includes the steps of thermally denaturing the cells in about 70% formamide/2×SSC at approximately 70° C., rinsing the resulting cells with distilled water, and permitting the rinsed cells to dry.

3. The method for determination of chromosomal orientation and strand direction of DNA sequences as described in claim 1, wherein said step of denaturing/solubilizing the halogenated nucleotide analogue-substituted strand includes the steps of immersing the cells in a high pH aqueous solution at approximately room temperature, rinsing the resulting cells with distilled water, and permitting the rinsed cells to dry.

4. The method for determination of chromosomal orientation and strand direction of DNA sequences as described in claim 1, wherein said step of denaturing/solubilizing the halogenated nucleotide analogue-substituted strand includes the steps of heating the cells, rinsing the resulting cells with distilled water, and permitting the rinsed cells to dry.

5. The method for determination of chromosomal orientation and strand direction of DNA sequences as described in claim 1, wherein the probe is stained subsequent to said step of hybridization.

6. The method for determination of chromosomal orientation and strand direction of DNA sequences as described in claim 1, wherein said step of inducing breaks in the halogenated nucleotide analogue-substituted strand is accomplished by the steps of staining the halogenated nucleotide analogue-substituted strand with Hoechst 33258 dye and irradiating the stained strand with uv radiation.

7. The method for determination of chromosomal orientation and strand direction of DNA sequences as described in claim 1, wherein said step of detecting the stained chromosomes includes observation of the stained chromosomes using a fluorescence microscope.

8. The method for determination of chromosomal orientation and strand direction of DNA sequences as described in claim 5, wherein said step of detecting the stained chromosomes includes observation of the stained chromosomes using a fluorescence microscope.

9. The method for determination of chromosomal orientation and strand direction of DNA sequences as described in claim 1, wherein the halogenated nucleotide analogue is selected from the group consisting of 5-bromo-2'-deoxyuridine and 5-bromo-2'-deoxycytidine.

10. The method for determination of chromosomal orientation and strand direction of DNA sequences as described in claim 1, wherein said step of denaturing/solubilizing the halogenated nucleotide analogue-substituted strand includes the steps of immersing the cells in a low pH aqueous solution at approximately room temperature, rinsing the resulting cells with distilled water, and permitting the rinsed cells to dry.

* * * * *